(12) United States Patent
Cheng et al.

(10) Patent No.: US 10,253,629 B2
(45) Date of Patent: Apr. 9, 2019

(54) TEST APPARATUS AND A TEST METHOD FOR THE WETTED PERIMETER OF COAL SEAM WATER INJECTION

(71) Applicant: Shandong University of Science and Technology, Qingdao (CN)

(72) Inventors: Weimin Cheng, Qingdao (CN); Zhen Liu, Qingdao (CN); Gang Wang, Qingdao (CN); Gang Zhou, Qingdao (CN); Lianjun Chen, Qingdao (CN); Wen Nie, Qingdao (CN); Lin Xin, Qingdao (CN); Yanbin Yu, Qingdao (CN); Guanhua Ni, Qingdao (CN); He Yang, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 255 days.

(21) Appl. No.: 15/359,751

(22) Filed: Nov. 23, 2016

(65) Prior Publication Data

US 2017/0146679 A1 May 25, 2017

(30) Foreign Application Priority Data

Nov. 24, 2015 (CN) .......................... 2015 1 0823642

(51) Int. Cl.
| | | |
|---|---|---|
| *E21F 5/02* | (2006.01) | |
| *G01V 3/20* | (2006.01) | |
| *E21B 21/16* | (2006.01) | |
| *E21F 11/00* | (2006.01) | |

(Continued)

(52) U.S. Cl.
CPC .............. *E21F 17/00* (2013.01); *E21B 21/16* (2013.01); *E21F 5/02* (2013.01); *E21F 11/00* (2013.01); *G01V 3/20* (2013.01); *G01N 33/222* (2013.01); *Y02A 90/342* (2018.01)

(58) Field of Classification Search
CPC . E21B 21/16; E21F 17/00; E21F 5/02; G01V 3/20; G01N 33/222; Y02A 90/342
See application file for complete search history.

(56) References Cited

U.S. PATENT DOCUMENTS

| | | | | |
|---|---|---|---|---|
| 2009/0308609 A1* | 12/2009 | Curole | .................... | E21B 43/20 166/275 |
| 2010/0276141 A1* | 11/2010 | Stegemeier | .............. | C10G 1/02 166/272.3 |
| 2011/0146982 A1* | 6/2011 | Kaminsky | ............... | E21B 43/24 166/272.2 |

* cited by examiner

*Primary Examiner* — Blake E Michener
(74) *Attorney, Agent, or Firm* — Buchanan Ingersoll & Rooney PC

(57) ABSTRACT

Described are a test apparatus and a test method for the wetted perimeter of coal seam water injection. In the test apparatus, a columnar insulator is provided between an upper electrode and a lower electrode, circular insulating tapes are located at the outer edges of the upper electrode and the lower electrode, a circular reverse osmosis membrane is provided at the middle of the circular insulating tape, the upper electrode, lower electrode, circular insulating tapes and circular reverse osmosis membrane form an enclosed chamber which is filled with solid sodium chloride, and cotton yarns are packed among the upper resin backing plate, lower resin backing plate, circular insulating tapes and the inner walls of water permeable perforated pipes. The upper electrode is provided with an electrode lead which passes through the columnar insulator, the lower electrode and the lower resin backing plate and goes out from the tail connecting end.

5 Claims, 2 Drawing Sheets

(51) Int. Cl.
*E21F 17/00* (2006.01)
*G01N 33/22* (2006.01)

TEST APPARATUS AND A TEST METHOD FOR THE WETTED PERIMETER OF COAL SEAM WATER INJECTION

TECHNICAL FIELD

The present disclosure relates to the field of mine safety and environmental engineering, more specifically relates to a test apparatus and a test method for the wetted perimeter of coal seam water injection.

BACKGROUND

With the increase in coal mining depth, the ground stress and gas pressure of the coal seams increase gradually, the permeability of the coal seams drastically decreases, the rockbursts, coal and gas outbursts and other power disasters of the coal seams are becoming increasingly serious, and especially extremely soft coal seams that have been subject to tectonic destruction lead to the increase of the danger of the coal dust disaster. At present, the coal seam water injection techniques are frequently utilized in China to prevent and control rockbursts, coal and gas outburst, coal dust and other disasters; different water injection pressures and modes are used depending on different disaster characteristics, these techniques include low and medium pressure water injection wetting, high pressure water injection, ultra-high pressure water injection fracturing and other water injection techniques with different pressures and further comprise static pressure water injection, dynamic pressure water injection (pulse fracturing) and other water injection techniques in different modes. After various water injection measures are taken on site, the effectiveness of coal seam water injection is often investigated, and especially the wetted perimeter of the coal seam water injection needs to be determined in the field of dust prevention and control. At present, for the existing investigation method, the moisture content is determined mainly by means of sampling the coal on site after water injection so as to determine the wetted perimeter of coal seam water injection, the moisture in the coal fissure in the test point area gets lost in advance owing to the influence of the investigation boreholes, resulting in large test errors of coal moisture content when this method is used to test the moisture content, and for this method, the samples are taken and tested after completion of water injection, resulting in failure to reflect the dynamic penetration process of coal seam water injection, thus leading to failure to provide adequate scientific reference for the optimization of coal seam water injection parameters.

SUMMARY OF THE DISCLOSURE

In light of the deficiencies of the above-mentioned art, the present disclosure aims at providing a test apparatus and a test method for the wetted perimeter of coal seam water injection, enriching the investigation means of the wetted perimeter of the coal seam water injection and providing scientific bases for the optimization of coal seam water injection process parameters.

To solve the above-mentioned technical problems, the present disclosure provides:

A test apparatus for the wetted perimeter of coal seam water injection which comprises a water permeable perforated pipe, the top of the water permeable perforated pipe is provided with a tapered end while the bottom of the water permeable perforated pipe is provided with the tail connecting end, the upper resin backing plate is located at the lower surface of the tapered end while the lower resin backing plate is located at the upper surface of the tail connecting end, the upper electrode is provided on the upper resin backing plate while the lower electrode is provided on the lower resin backing plate, the upper resin backing plate and the upper electrode are symmetrically arranged with the lower resin backing plate and the lower electrode respectively, a columnar insulator is provided between the upper electrode and the lower electrode, circular insulating tapes are located at the outer edges of the upper electrode and the lower electrode, the circular reverse osmosis membrane is provided at the middle of the circular insulating tape, the upper electrode, lower electrode, circular insulating tape and circular reverse osmosis membrane form an enclosed chamber which is filled with solid sodium chloride, and cotton yarns are packed among the upper resin backing plate, lower resin backing plate, plate circular insulating tapes and the inner walls of water permeable perforated pipes; the upper electrode is provided with an electrode lead which passes through the columnar insulator, the lower electrode, the lower resin backing plate and goes out from the tail connecting end.

In one embodiment, the water permeable perforated pipe is provided with several water permeable holes which are evenly distributed.

In another embodiment, the electrode lead is sealed with sealant at the place where it passes through the small hole of the tail connecting end which is placed onto the PVC pipe.

In another embodiment, the electrode lead is connected with an electrical conductivity detector.

A test method using the test apparatus, which comprises the following steps:

A. drilling construction is carried out in the coal roadway to drill a first investigation borehole, a second investigation borehole and a third investigation borehole respectively, the investigation boreholes are parallel to the water injection borehole in the coal roadway, a first investigation borehole and a third investigation borehole are located at one side of the water injection borehole and a second investigation borehole is located at the other side of the water injection borehole, a first investigation borehole, a third investigation borehole and a second investigation borehole are 2, 6 and 4 meters away from the water injection borehole respectively, the investigation boreholes are constructed through pneumatic dust removal and 76 mm in diameter, the termination positions of a first investigation borehole and a third investigation borehole are staggered, the test apparatus is placed to the bottom of the borehole after completion of each borehole, the borehole is sealed with polyurethane and electrode lead goes out from the borehole head;

B. the electrical conductivity detector is connected with the test apparatus in each investigation borehole, when the electrical conductivity of the test apparatus in each investigation borehole is zero, it can be judged that the investigation borehole has been laid successfully, the water injection borehole can be constructed and sealed, and then water is injected into the coal seam, during which, the electrical conductivity of a first investigation borehole is monitored;

C. when the pressure water reaches a first investigation borehole, water will pass through the water permeable perforated pipe and cotton yarns, run into the circular reverse osmosis membrane and rapidly dissolve the solid sodium chloride in the enclosed chamber, forming the strong electrolyzed aqueous solution of sodium chloride, the coal solid particles mixed in the pressure water are blocked off by the cotton yarns and circular reverse osmosis membrane, and when the electrical conductivity of the test apparatus in a first investigation borehole rises abruptly, it can be judged that the wetted perimeter of radial water injection reaches 2 meters;

D. the variation of the electrical conductivity value of a second investigation borehole and a third investigation borehole is observed sequentially in the process of water injection, the extreme wetted perimeter of coal seam water injection and the dynamic distribution characteristics of pressure water in the process of water injection are obtained according to the test result.

The present disclosure provides a test apparatus and a test method for the wetted perimeter of coal seam water injection, which determine the wetted perimeter of coal seam water injection through testing the electrical conductivity of the solution formed after the solid NaCl is solved by the moisture of coal body based on the characteristic of solid NaCl acting as a non-conductive strong electrolyte. This effectively avoids large test errors caused by moisture loss of the coal fissure in the test point area, thus resulting in an inaccurate scope of investigation when the moisture content is tested with the conventional investigation methods, provides a novel technical solution for the investigation over the dynamic wetted perimeter of the coal seam water injection, enriches the means of investigation over the wetted perimeter of coal seam water injection, improves the effectiveness of the disaster prevention of the coal seam water injection and safeguards safe and efficient mining of the mine shafts.

As shown in these figures, 1—test apparatus, 2—polyurethane seal, 3—PVC pipe, 4—coal roadway, 5—electrode lead, 6—3# investigation borehole, 7—coal seam, 8—1# investigation borehole, 9—water injection borehole, 10—2# investigation borehole, 11—electrical conductivity detector, 12—cotton yarn, 13—solid sodium chloride, 14—water permeable perforated pipe, 15—water permeable hole 16—tapered end, 17—upper resin backing plate, 24—lower resin backing plate, 18—upper electrode, 25—lower electrode, 19—circular reverse osmosis membrane, 20—columnar insulator, 21—circular insulating tape, 22—sealant, 23—tail connecting end.

DETAILED DESCRIPTION

The present disclosure provides a test apparatus and a test method for the wetted perimeter of coal seam water injection and is here further explained for further clarity of the objective, technical solution and effectiveness of the present disclosure. It shall be understood that the specific embodiments as described here are merely used to explain the present invention and are not intended to limit the present invention.

Figure 1:
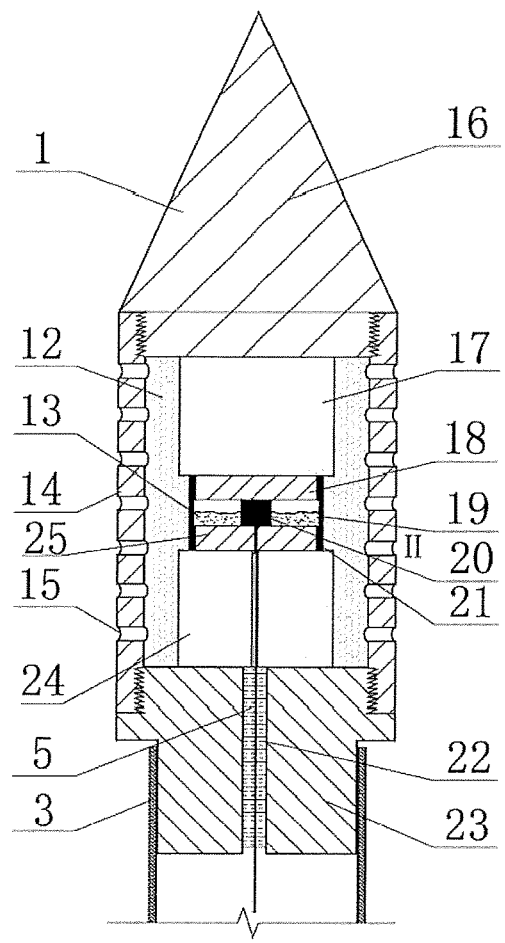
FIG. 1 illustrates a schematic view of the structure of the test apparatus in an embodiment.
Figure 2:
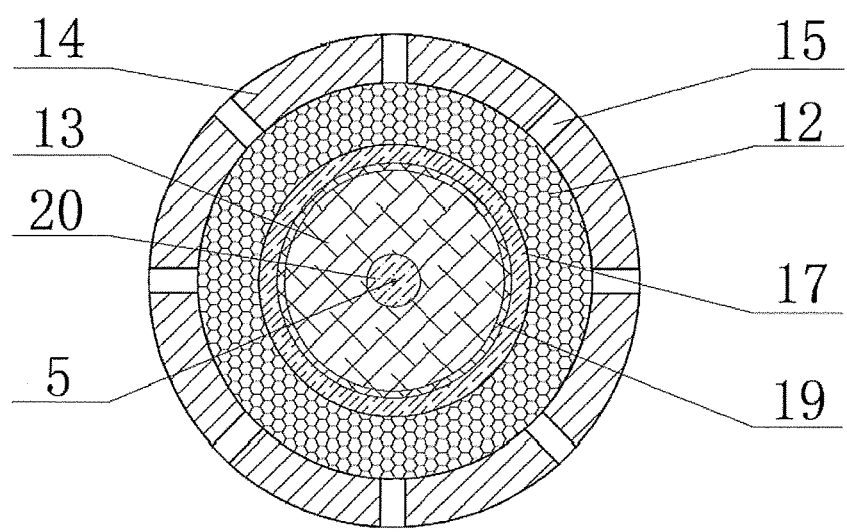
FIG. 2 illustrates a schematic view of the structure of the enclosed chamber in an embodiment.
Figure 3:
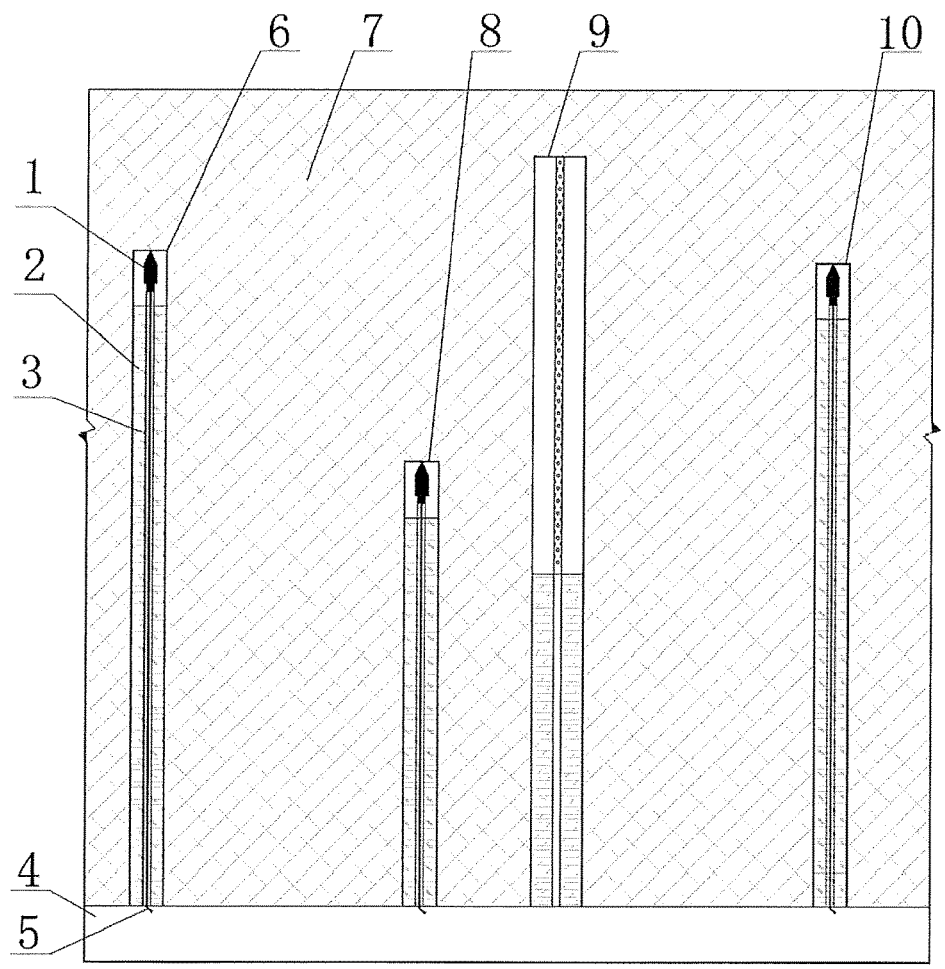
FIG. 3 illustrates a schematic layout of the test method in an embodiment.
Figure 4:
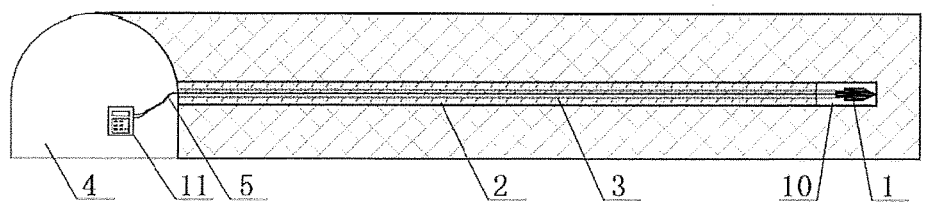
FIG. 4 illustrates a schematic layout of one investigation borehole in an embodiment.

The present disclosure provides a test apparatus for the wetted perimeter of coal seam water injection, as shown in FIGS. 1 & 2, which comprises a water permeable perforated pipe 14, wherein the top of the water permeable perforated pipe 14 is provided with a tapered end 16 while the bottom of the water permeable perforated pipe 14 is provided with the tail connecting end 23, the upper resin backing plate 17 is located at the lower surface of the tapered end 16 while the lower resin backing plate 24 is located at the upper surface of the tail connecting end 23, the upper electrode 18 is provided on the upper resin backing plate 17 while the lower electrode 25 is provided on the lower resin backing plate 24, the upper resin backing plate 17 and the upper electrode 18 are symmetrically arranged with the lower resin backing plate 24 and the lower electrode 25 respectively, for clarity, the upper resin backing plate 17 and the lower resin backing plate 24 are is symmetric to each other and the upper electrode 18 and the lower electrode 25 are symmetric to each other by taking the under-mentioned columnar insulator 20 as their reference of symmetry. The columnar insulator 20 is provided between the upper electrode 18 and the lower electrode 25, circular insulating tapes 21 are located at the outer edges of the upper electrode 18 and the lower electrode 25, the circular reverse osmosis membrane 19 is provided at the middle of the circular insulating tape 21, has the single-direction water permeable function and is capable of preventing the solute overflow from the NaCl solution. The upper electrode 18, lower electrode 25, circular insulating tape 21 and circular reverse osmosis membrane 19 form an enclosed chamber which is filled with solid sodium chloride 13, and cotton yarns 12 are packed among the upper resin backing plate 17, lower resin backing plate 24, plate circular insulating tapes 21 and the inner walls of water permeable perforated pipe 14 and is capable of removing, through filtration, the impurities in the high pressure water for injection; the upper electrode 18 is provided with an electrode lead 5 which passes through the columnar insulator 20, the lower electrode 25 and the lower resin backing plate 24 and goes out from the tail connecting end 23 and is used to connect the external instruments.

Furthermore, the water permeable perforated pipe 14 is provided with several water permeable holes 15 which are evenly distributed and help the water run into the water permeable perforated pipe 14 without difficulties. Moreover, the electrode lead 5 is sealed with sealant at the place where it passes through the small hole of the tail connecting end 23 which is placed onto the PVC pipe 3 so that the test apparatus is arranged in the corresponding investigation borehole. Additionally, the electrode lead 5 is connected with an electrical conductivity detector 11 which makes it possible to visually observe the variation of electrical conductivity of the corresponding investigation borehole.

The present disclosure also provides a test method using the test apparatus, which comprises the following steps:

Step A: Drilling construction is carried out in the coal roadway 4 to drill a first investigation borehole 8, a second investigation borehole 10 and a third investigation borehole 6 respectively which are renamed 3# investigation borehole 6, 1# investigation borehole 8 and 2# investigation borehole 10 respectively in the following text, the investigation boreholes are parallel to the water injection borehole 9 in the coal roadway 4, a first investigation borehole 8 and a third investigation borehole 6 are located at one side of the water injection borehole 9 and a first investigation borehole 8 is less in height than a third investigation borehole 6, a second investigation borehole 10 is located at the other side of the water injection borehole 9, a first investigation borehole 8, a third investigation borehole 6 and a second investigation borehole 10 are 2, 6 and 4 meters away from the water injection borehole 9 respectively, the investigation boreholes are constructed through pneumatic dust removal and 76 mm in diameter, the termination positions of a first investigation borehole 8 and a third investigation borehole 6 are staggered, the test apparatus is placed to the bottom of the borehole after completion of each borehole, the borehole is sealed with polyurethane seal 2 and the electrode lead 5 goes out from the borehole head;

Step B: The electrical conductivity detector 11 is connected with the test apparatus 1 in each investigation borehole, when the electrical conductivity of the test apparatus 1 in each investigation borehole is zero, it can be judged that the investigation borehole has been laid successfully, the water injection borehole can be constructed and sealed, and then water is injected into the coal seam, during which, the electrical conductivity of a first investigation borehole 8 is monitored;

Step C: When the pressure water reaches a first investigation borehole 8, water will pass through the water permeable perforated pipe 14 and cotton yarns 12, run into the circular reverse osmosis membrane 19 and rapidly dissolve the solid sodium chloride 13 in the enclosed chamber, forming the strong electrolyzed aqueous solution of sodium chloride, the coal solid particles mixed in the pressure water are blocked off by the cotton yarns 12 and circular reverse osmosis membrane 19 which has the single-direction water permeable function and is capable of preventing the solute overflow from the sodium chloride solution, and when the electrical conductivity of the test apparatus 1 in a first investigation borehole 8 rises abruptly, it can be judged that the wetted perimeter of radial water injection reaches 2 meters;

Step D: The variation of the electrical conductivity value of a second investigation borehole 10 and a third investigation borehole 6 is observed sequentially in the process of water injection, the extreme wetted perimeter of coal seam water injection and the dynamic distribution characteristics of pressure water in the process of water injection are obtained according to the test result.

What is claimed is:

1. A test apparatus for wetted perimeter of coal seam water injection which comprises a water permeable perforated pipe, wherein:
    a top of the water permeable perforated pipe is provided with a tapered end while a bottom of the water permeable perforated pipe is provided with a tail connecting end,
    an upper resin backing plate is located at a lower surface of the tapered end while a lower resin backing plate is located at an upper surface of the tail connecting end,
    an upper electrode is provided on the upper resin backing plate while a lower electrode is provided on the lower resin backing plate,
    the upper resin backing plate and the upper electrode are symmetrically arranged with the lower resin backing plate and the lower electrode respectively,
    a columnar insulator is provided between the upper electrode and the lower electrode,
    a first circular insulating tape is located at an outer edge of the upper electrode and a second circular insulating tape is located at an outer edge of the lower electrode,
    a circular reverse osmosis membrane is provided immediately between the first and second circular insulating tapes,
    the upper electrode, lower electrode, first and second circular insulating tapes and circular reverse osmosis membrane form an enclosed chamber which is filled with solid sodium chloride, and
    cotton yarns are packed among the upper resin backing plate, lower resin backing plate, first and second circular insulating tapes and inner walls of the water permeable perforated pipe;
    the upper electrode is provided with an electrode lead which passes through the columnar insulator, the lower electrode and the lower resin backing plate, and goes out from the tail connecting end.

2. The test apparatus according to claim 1, wherein the water permeable perforated pipe is provided with a plurality of water permeable holes which are evenly distributed.

3. The test apparatus according to claim 1, wherein the electrode lead is sealed with sealant at a place where it passes through a hole of the tail connecting end which is placed onto a PVC pipe.

4. The test apparatus according to claim 1, wherein the electrode lead is connected with an electrical conductivity detector.

5. A test method comprising the following steps:
    a. drilling construction is carried out in a coal roadway to drill a first investigation borehole, a second investigation borehole and a third investigation borehole respectively, wherein the first, second and third investigation boreholes are parallel to a water injection borehole in the coal roadway, the first investigation borehole and the third investigation borehole are located at one side of the water injection borehole and the second investigation borehole is located at the other side of the water injection borehole, the first investigation borehole, the third investigation borehole and the second investigation borehole are 2, 6 and 4 meters away from the water injection borehole respectively, the investigation boreholes are constructed through pneumatic dust removal and are 76 mm in diameter, termination positions of the first investigation borehole and the third investigation borehole are staggered, the test apparatus according to claim 1 is synchronously placed to the bottom of the 3 investigation boreholes after completion of each borehole, the borehole is sealed with polyurethane and the electrode lead goes out from the borehole head;
    b. an electrical conductivity detector is connected with the test apparatus in each investigation borehole, wherein when electrical conductivity of the test apparatus in each investigation borehole is zero, the investigation borehole has been laid, the water injection borehole is constructed and sealed with polyurethane, and then water is injected into the coal seam, during which, electrical conductivity of the first investigation borehole is monitored;
    c. when pressurized water reaches the first investigation borehole, the water passes through the water permeable perforated pipe and cotton yarns, runs into the circular reverse osmosis membrane and dissolves the solid sodium chloride in the enclosed chamber, forming an electrolyzed aqueous solution of sodium chloride, coal solid particles mixed in the pressurized water are blocked off by the cotton yarns and circular reverse osmosis membrane, and when the electrical conductivity of the test apparatus in the first investigation borehole rises, a wetted perimeter of radial water injection reaches 2 meters;
    d. variation of an electrical conductivity value of the second investigation borehole and the third investigation borehole is observed sequentially in the process of water injection.

* * * * *